(12) United States Patent
Levendowski et al.

(10) Patent No.: US 8,333,696 B2
(45) Date of Patent: Dec. 18, 2012

(54) SYSTEMS AND METHODS FOR AUTOMATED PREDICTION OF RISK FOR PERIOPERATIVE COMPLICATIONS BASED ON THE LEVEL OF OBSTRUCTIVE SLEEP APNEA

(75) Inventors: Daniel J. Levendowski, Carlsbad, CA (US); Philip R. Westbrook, Carlsbad, CA (US); Chris Berka, Carlsbad, CA (US)

(73) Assignee: Watermark Medical, Inc., Boca Raton, FL (US)

( * ) Notice: Subject to any disclaimer, the term of this patent is extended or adjusted under 35 U.S.C. 154(b) by 770 days.

(21) Appl. No.: 11/955,185

(22) Filed: Dec. 12, 2007

(65) Prior Publication Data
US 2008/0146893 A1 Jun. 19, 2008

Related U.S. Application Data

(60) Provisional application No. 60/869,795, filed on Dec. 13, 2006.

(51) Int. Cl.
*A61B 5/00* (2006.01)
(52) U.S. Cl. ............... 600/300; 705/2; 705/3; 600/529; 128/920
(58) Field of Classification Search ............. 600/300, 600/301, 529; 340/571.1; 128/920; 705/2–3
See application file for complete search history.

(56) References Cited

U.S. PATENT DOCUMENTS

| | | | |
|---|---|---|---|
| 5,081,447 A | 1/1992 | Echols | |
| 5,381,801 A | 1/1995 | McShane | |
| 5,447,161 A | 9/1995 | Blazek et al. | |
| 6,223,064 B1 * | 4/2001 | Lynn et al. | 600/324 |
| 6,600,949 B1 | 7/2003 | Turcott | |
| 6,641,571 B2 | 11/2003 | Redmond et al. | |
| 6,811,538 B2 | 11/2004 | Westbrook et al. | |
| 6,970,792 B1 | 11/2005 | Diab | |
| 7,081,095 B2 | 7/2006 | Lynn | |
| 7,117,028 B2 | 10/2006 | Bardy | |
| 7,311,666 B2 * | 12/2007 | Stupp et al. | 600/300 |
| 7,691,067 B2 | 4/2010 | Westbrook | |

(Continued)

OTHER PUBLICATIONS

Stierer, T. et al., "Demographics and Diagnosis of Obstructive Sleep Apnea", Anesthesiology Clinics of North America, 23 (2005) 405-420.*

(Continued)

*Primary Examiner* — Sam Yao
*Assistant Examiner* — Marie Archer
(74) *Attorney, Agent, or Firm* — Fiala & Weaver P.L.L.C.

(57) ABSTRACT

A system for predicting risk for perioperative complications is described including a user device for receiving a set of risk factors to determine perioperative complications for a patient including patient data useful to determine the likelihood of obstructive sleep apnea. The system also includes an acquisition module to receive data from an obstructive sleep apnea sleep study of the patient. Further a determination module can determine the severity of obstructive sleep apnea for the patient. The system can also include an analysis module having a predictive model that incorporates one or more prediction equations for predicting perioperative complications derived from one or more databases having multiple patient data relevant to predict perioperative complications. The analysis module can be configured to apply the one or more prediction equations to the set of risk factors and the severity of obstructive sleep apnea for the patient in order to identify perioperative complication risks of that patient and to generate a perioperative complications report for the patient.

23 Claims, 6 Drawing Sheets

U.S. PATENT DOCUMENTS

| | | | | |
|---|---|---|---|---|
| 7,717,848 | B2* | 5/2010 | Heruth et al. | 600/300 |
| 2002/0184050 | A1* | 12/2002 | Papageorge | 705/2 |
| 2004/0015337 | A1* | 1/2004 | Thomas et al. | 703/11 |
| 2005/0234313 | A1* | 10/2005 | Rowlandson et al. | 600/301 |
| 2006/0129427 | A1* | 6/2006 | Wennberg | 705/2 |
| 2007/0214013 | A1* | 9/2007 | Silverman | 705/2 |
| 2007/0282177 | A1* | 12/2007 | Pilz | 600/301 |

OTHER PUBLICATIONS

Lew, E. et al., "Outpatient preaneaesthesia evaluation clinics", Singapore Medical Journal, 45 (11), 2004, 509-516.*

Walker, G. A., "Common Statistical Methods for Clinical Research with SAS Examples", Second Edition, Jul. 15, 2002, SAS Publishing. p. 1-7.*

AARC Clinical Practical Guideline for Polysomnography, Respiratory Care, 1995, 40 (12):1336-1343.*

Peng J. C-Y., et al. "An Introduction to Logistic Regression Analysis and Reporting", 2002, "The Journal of Educational Research", Sep./Oct. 2002, vol. 96, No. 1, p. 3-14.*

Parker, B. M., et al., "Redefining the preoperative evaluation process and the role of the anesthesiologist", Journal of Clinical Anesthesia (2000) 12:350-356.*

Jian, S. "Perioperative treatment of patients with obstructive sleep apnea", 2004, Curr Opin Pulm Med 10:482-488.*

Practice Guidelines for Perioperative Management, Anesthesiology 2006; 104:1081-1093.*

Roberts, A. J. et al in "Mortality, Morbidity and Cost-Accounting Related to Coronary Artery Bypass Graft Surgery in the Elderly", The Annals of Thoracic Surgery, 1985; 39:426-432.*

Penzel, T. et al. In "Effect of sleep position and sleep stage on the collapsibility of the upper airways in patients with sleep apnea", Sleep, vol. 24, No. 1, 2001, p. 90-95.*

A Report by the American Society of Anesthesiologists Task Force on Perioperative Management of Patients with Obstructive Sleep Apnea, Practice Guidelines for the Perioperative Management of Patients with Obstructive Sleep Apnea. Anesthesiology, 2008. 104(5); p. 1081-1093.

Alemohammad, M., Z Khan, M Snetkar, S Mirkhani, Ghorbandaie-Poure I., Pressure measurements during cardiac surgery—internal jugular vs. central venous. Middle East J Anestesiol. 2005; 18(2)367-65.

Argod J. Pepin J, Smith R. Levy P. Comparison of Esophageal Pressure with Pulse Transit Time as a measure of respiratory effort for scoring obstructive nonapneic respiratory events. Am J Respir Crit Care Med vol. 162 (2000) 87-93.

Aurell, J. and D. Elmqvist, Sleep in the surgical intensive care unit: continuous polygraphic recording of sleep in nine patients receiving postoperative care. Sr Med J (Clin Res Ed), 1985, 290(6474): p. 1029-32.

Benumof, J.L., Obstructive sleep apnea in the adult obese patient: implications for airway management. Anesthesiology Clinics of North America, 2002, 20(4): p. 789-811.

Benumof, J.L., Obesity, sleep apnea, the airway, and anesthesia, Current Opinion in Anaesthesiology, 2004. 17(1): p. 21-30.

Brown, K: Intermittent Hypoxia and the Practice of Anesthesia. Anesthesiology, 2009 110(4). p. 922-7.

Cannesson M, Besnard C, Durand PG, Bohe J, Jacques D. Relation between respiratory variations in pulse oximetry plethysmographic waveform amplitude and arterial pulse pressure in ventilated patients. Crit Care. Oct. 5, 2005;9(5):R562-8. Epub Aug. 23, 2005.

Catley, DM., et al., Pronounced, episodic oxygen desaturation in the postoperative period: Its association with ventilatory pattern and analgesic regimen. Anesthesiology, 1985. 63(1): p. 20-8.

Chung et al., A Systemic Review of Obstructive Sleep Apnea and Its Implications for Anesthesiologists, Ambulatory Anesthesiology, vol. 107, No. 5, Nov. 2008, pp. 1543-1563.

Cox P. Johnson JO, Tobias JD. Measurement of central venous pressure from a peripheral intravenous catheter in the lower extremity. South Med J. Jul. 2005;98(7):698-702.

Cronin, A. et al, Opioid inhibition of rapid eye movement sleep by a specific mu receptor agonist. Br J Anaesth, 1995, 74(2): p. 188-92.

Den Herder, Cindy et al., Risks of General Anaesthesia in People with Obstructive Sleep Apnoea, BMJ, vol. 329, Oct. 23, 2004, pp. 955-959 and 1 cover sheet.

Deutscher, R., et al., OSA protocol promotes safer care. Anesthesia Patient Safety Foundation Newsletter 2002-2003: p. 58-60.

Ellis, B W. and H.A. Dudley, Some aspects of sleep research in surgical stress. J Psychosom Res, 1976. 20(4):2 303-8.

Farre R, Montserrat JM, Navejas D. Noninvasive monitoring of respiratory mechanics during sleep. Eur Respir J. Dec. 2004;24(16):1052-60.

Finkel, K., et al., Obstructive Sleep Apnea: The Silent Pandemic. in ASA Annual Meeting. 2006, Chicago, IL: 1 page.

Finkel. K., et al., The Silent Perioperative Pandemic. Sleep Review, 2006, 7(4): p. 56-60.

Foo J, Wilson S. Bradley A. Williams G, Harris M, Cooper D. Use of pulse transit time to distinguish respiratory events from tidal breathing in sleeping children. Chest 2005: 12 3013-3019.

Foo JY., Wilson SJ. Estimation of breathing interval from the photoplethysmographic signals in children. Physiol Meas. Dec. 2005;26(6):1049-58. Epub Oct. 31, 2005.

Gali, B.: Identification of Patients at Risk for Postoperative Respiratory Complications Using a Preoperative Obstructive Sleep Apnea Screening Tool and Postanesthesia Care Assessment. Anesthesiology. 2009 110(4). p. 869-77.

Gali, Ehargavi et al., Management Plan to Reduce in Perioperative Care of Patients with Presumed Obstructive Sleep Apnea Syndrome, JCSM Journal of Clinical Sleep Medicine, vol. 3, No. 6, 2007, pp. 582-588.

Gentil, B., et al., Enhancement of postoperative desaturation in heavy snorers. Anesth Analg 1995, 81(2): p. 389-92.

Gisolf J, Van Lieshout, J, Van Heusden K, Pott F, Stok W, Karemaker J. Human cerebral venous outflow pathway depends on posture and central venous pressure. J Physiol 560.1 (2004) 317-327.

Gupta, R., et al., Postoperative complications in patients with obstructive sleep apnea syndrome undergoing hip or knee replacement: a case-control study. Mayo Clinic Proceedings, 2001. 76: p. 897-905.

Haba-Rubio J. Darbellay G, Herrmann FR, Frey JG, Fernandes A, Vesin JM, Thiran JP, Tschopp JM. Obstructive sleep apnea syndrome: effect of respiratory events and arousal on pulse wave amplitude measured by photoplethysmography in NREM sleep. Sleep Breath (2005) 9: 73-81.

International Search Report/Written Opinion issued in PCTUS2007071242 on Mar. 13, 2008, 11 pages.

Johansson A, Oberg PA. Esfimation of respiratory volumes from the photoplethysmographic signal. Part I: Experimental results. Med Biel Eng Comput Jan. 1999:37(1):42-7.

Johansson A, Oberg PA. Estimation of respiratory volumes from the photoplethysmographic signal. Part 2: A model study, Med Biot Eng Comput. Jan. 1999;37(1):48-53.

Johansson A, Stromberg T. Influence of tidal volume and thorace-andominal separation on the respiratory induced variation of the photoplethysmogram, J Clin Monit Comput. 2000:16(8):575-81.

Johansson A. Neural network for photoplethysmographic respiratory rate monitoring, Med Biol Eng Comput., May 2003:41(3):242-8.

Kaw, R., et al., Unrecognized Sleep Apnea in the Surgical Patient: Implications for the Perioperative Setting. Chest, 2006, 129(1): p. 198-205.

Keifer, J., et al., Sleep Disruption and Increased Apneas after Pontine Microinjection of Morphine. Anesthesiology, 1992, 77(5): p. 973-82.

Kheterpal, Sadnin et al Prediction and Outcomes of Impossible Mask Ventilation, Anesthesiology, vol. 110, No. 4, Apr. 2009, pp, 891-897.

Knill, R., et al., Anesthesia with Abdominal Surgery Leads to intense REM Sleep during First Postoperative Week. Anesthesiology, 1990, 73(1): p. 52-61.

Kushida C, Gidcomini A, Lee M. Guilieminault C, Dement W. Technical protocol for the use of esophageal manometry in the diagnosis of sleep-related breathing disorders. Sleep Med 3(2002) 163-173.

Leonard P, Grubb NR, Addison PS, Clifton D, Watson JN. An algorithm for the detection of individual breaths from the pulse oximeter waveform. J Clin Monit Comput. Dec. 2004;18(5-6):309-12.

Lickteig, Carla et al., Risks of OSA and Anesthesia, Sleep Review, Jan./Feb. 2003, 5 pages.

Loadsman, J. and D. Hillivian, Anaesthesia and sleep apnoea. British Journal of Anaesthesia, 2001. 86(2): p. 254-266.

Lofsky, Ann, Sleep apnea and narcotic postoperative pain medication: a morbidity and mortality risk, Anesthesia Patient Safety Foundation Newsletter. Summer 2002:24-25.

Magder S. How to use central venous pressure measurements. Curr Opin Crit Care, Jun. 2005;11(3):264-70.

Mannheimer P, O'Neil M, Konecny E, The influence of large subcutaneous blood vessels on pulse oximetry. J Clin Monitor Comput 18:179-188, 2004.

Nakajima K. Tamura T, Mike H. Monitoring the heart and respiratory rates by photoplethysmography using a digital filtering technique. Med Eng Phys 1996 1 8(5) 365-372.

Neligan, Patrick J. et al., Continuous Positive Airway Pressure via the Boussignac System Immediately after Extubation Improves Lung Function in Morbidly Obese Patients with Obstructive Sleep Apnea Undergoing Laparoscopic Bariactric Surgery, Anesthesiology, vol. 110, No. 4, Apr. 2009, pp. 878-884.

Nilsson et al., Age and gender do not influence the ability to detect respiration by photoplethysmography, J Clin Monit Comput Dec. 2006; 20(6), pp. 431-8. Epub Oct. 11, 2006.

Nilsson et al., Macrocircuiation is not the sole determinant of respiratory induced variations in the reflection mode photoplethysmographic signal, Physiol Meas, Nov. 2003; 24(4);925-37.

Nilsson et al., Monitoring of respiratory rate in postoperative care using a new photoplethysmogrephic technique, J Clin Monit Comput. 2000; 16(4):309-15.

Nilsson et al., Respiration can be monitored by photoplethysmography with high sensitivity and specificity regardless of anaesthesia and ventilatory mode. Acta Anaesthesioi Scand: Sep. 2005; 49(8): 1187-62.

Nilsson et al., Respiratory variations in the reflection mode onatoplethysmographic signal. Relationships to peripheral venous pressure. Med Biol Comput. May 2008:41(3)249-54.

Oliver, Z. and V. Hoffstein, Predicting effective continuous positive airway pressure, Chest, 2000. 117(4): p. 1061-4.

Orr, W.C. and M.L, Stahl, Sleep disturbances after open heart surgery. Am J Cardiol, 1977, 39(2): p. 196-201.

Pembrook, Linda High Risk for Sleep Apnear Found in Pain Patients on Opioids, Issue; Jun. 2006, vol. 32:06, 3 pages.

Pilcher, D., C Scheinkestei, G Snell, A Davey-Quinn, M Bailey, T Williams. High central venous pressure is associated with prolonged mechanical ventilation and increased mortality after lung transplantation, J Thorac Cardiovasc Surg. 2005;129(4):912-8.

Pitson D., Stradim J. Value of beat-to-beat blood pressure changes, detected by pulse transit time, in the management of obstructive sleep apnea/hypopnea syndrome. Eur Resir J 1998:12:685-692.

Ramachandran at al., A Meta-analysis of Clinical Screening Tests for Obstructive Steep Apnea, Anesthesiology, Vo. 110,, No, 4, Apr. 2009, pp. 928-939.

Reeder, M.K., et al., Late postoperative nocturnal dips in oxygen saturation in patients undergoing major abdominal vascular surgery, Predictive value of pre-operative overnight pulse oximetry. Anaesthesia, 1992. 47(2): p. 110-5.

Reeder, M.K., et al., Postoperative hypoxamia after major abdominal vascular surgery. Sr J Anaesth, 1992, 68(1): p. 23-6.

Reeder, M.K., et al., Postoperative obstructive sleep apnoea. Haemodynamic effects of treatment with nasal CPAP Anaesthesia, 1991. 46(10): p. 849-53.

Remmers, J.E., et al., Pathogenesis of upper airway occlusion during sleep. J Appl Physiol,: Respirat. Environ. Exercise Physiol., 1978. 44(6): p. 931-8.

Rock, P. and A. Passankante, Preoperative assessment pulmonary. Anesthesiology Clinics of North America, 2004, 22(1): p. 77-91.

Rosenberg, J. and H. Kemlet, Postoperative episodic oxygen desaturation in the sleep apnoea syndrome. Acta Anaestnesiol Scand, 1991. 35(4): p. 368-9.

Rosenberg, J., et al., Circadian variation in unexpected postoperative death. Br J Burg, 1992, 79(12) p. 1300-2.

Rosenberg, J., et al., Late postoperative nocturnal episodic hypoxamia and associated sleep pattern. Br J Anaesth, 1994. 72(2): p. 145-50.

Rosenberg-Adamsen, et al., Postoperative sleep disturbances: mechanisms and clinical implications. Br J Anaesth, 1996, 76(4): p. 552-9.

Sabers, C., et al.: The diagnosis of obstructive sleep apnea as a risk factor for unaticipated admissions in outpatient surgery. Anesth Analg. May 2003;96(5):1328-35.

Sasse, S.A,, et al., Timing of Changes in Oxyhemogiobin Saturation Resulting from Breath Holding. Sleep Medicine, 2006. 7 (S2): p. 546-7.

Shepard JW Jr, Pevernagie DA, Sanson AW, Daniels BK, Sheedy PF. Effects of changes in central venous pressure on upper airway size in patients with obstructive sleep apnea. Am J Respir Crit Care Med. Jan. 1996;153(1):250-4.

Standards and Practice Committee of the American Sleep Disorders Association, ASDA Standards of Practice, Practice Parameters for the Use of Portable Recording in the Assessment of Obstructive Sleep Apnea., Sleep, 1994 17(4). p. 372-377.

Teng XF, Zhang YT. The effect of contacting force on photoplethvsmographic signals. Physiol Meas. Oct. 2004;25(5):1323-35.

Waldemar Carlo et al. Alae nasi activation (nasal flaring) decreases nasal resistance in preterm infants. Pediatric vol. 72, Issue 3, pp. 338-343.

Warner, David S. et al., Obstructive Sleep Apnea of Obese Adults, Anesthesiology, vol. 110, No. 4, Apr. 2009, pp. 908-921.

Westbrook P. at el. Predicting Effective Continuous Positive Airway Pressure (CPAP) based on Laboratory Titration and Auto-titrating CPAP, 8th World Congres, on OSA, Sleep Medicine. vol. 7, Suppl. 2. 2006, 2 pages.

Westbrook P, et al., Predicting Treatment Outcomes for Oral Appliance Therapy for Sleep Apnea using Pre-treatment in-home Sleep Studies, 8th World Congress on OSA. Sleep Medicine. vol. 7, Suppl. 2. 2006, p. 1-2.

Westbrook, P., et al., Validation of an Apnea Risk Evaluation Questionnaire in America Thoracic Society International Conference. 2005. San Deigo, CA. 2 pages.

Westbrook, P., et al., Description and Validation of the Apnea Risk Evaluation System: A Novel Method to Diagnose Sleep Apnea-Hypopnea in the Home Chest, 2005, 128(4): p. 2168-75.

Wilson, Kerryn et al., Can Assessment for Obstructive Sleep Apnea Help Predict Postadenotonsillectomy Respiratory Complications, Anesthesiology, vol. 96, No. 2, Feb. 2002, pp. 313-322.

Young, T., et al., Epidemology of Obstructive Sleep Apnea: A Population Health Perspective. Am J Respir Crit Care Med, 2002. 165(9): p. 1217-39.

* cited by examiner

SYSTEMS AND METHODS FOR AUTOMATED PREDICTION OF RISK FOR PERIOPERATIVE COMPLICATIONS BASED ON THE LEVEL OF OBSTRUCTIVE SLEEP APNEA

RELATED APPLICATIONS

This application claims the benefit of the priority of U.S. Provisional Application No. 60/869,795, filed Dec. 13, 2006, which is incorporated herein by reference in its entirety.

FIELD OF THE INVENTION

The present invention relates generally to a hospital monitoring system, and, in particular to an apnea risk evaluation system for automated prediction of risk for perioperative complications.

BACKGROUND OF THE INVENTION

Obstructive sleep apnea (OSA) is characterized by periodic, partial or complete obstruction of the upper airway during sleep. The underlying pathophysiology of OSA is complex. However, it is generally accepted that the stability and patency of the upper airway is dependent upon the action of oropharyngeal dilator muscles, which are normally activated during each inspiration. These muscles can increase their activity to overcome obstruction during wakefulness, but the normal decrease in activity that occurs with sleep can allow the susceptible airway to collapse. Return of airway muscle activity appears to require either arousal, or a change of brain state to a lighter stage of sleep. Given the choice between sleeping and breathing, the un-medicated brain will choose breathing. The repetitive asphyxia causes repetitive arousals, resulting in fragmented sleep and daytime somnolence. Airway obstruction also causes sleep-associated oxygen desaturation (Chronic Intermittent Hypoxia, or CIH), episodic hypercarbia, and cardiovascular dysfunction.

The prevalence of OSA in adults in Western countries is estimated to be 5%. See Young, T., P. E. Peppard, and D. J. Gottlieb in their article entitled "Epidemiology of obstructive sleep apnea: a population health perspective", published in American Journal of Respiratory and Critical Care Medicine, 2002, 165(9): p. 1217-39. This number is likely to increase as the population becomes older and more obese. The prevalence of obstructive sleep apnea in surgical patients has been estimated to be 1-9%, and may be even more common in certain populations. See Kaw, R., F. Michota, A. Jaffer, S. Ghamande, D. Auckley, and J. Golish in their article entitled "Unrecognized sleep apnea in the surgical patient: implications for the perioperative setting," published in Chest, 2006. 129(1): p. 198-205. A recently completed study at Washington University found that the prevalence of OSA (defined as AHI≧5) in surgical patients was more than 19%. See Finkel, K., L. Saager, E. Safarzadeh, M. Bottros, and M. Avidan in their article entitled "Obstructive Sleep Apnea: The Silent Pandemic," presented in the ASA Annual Meeting, 2006, Chicago, Ill.

Patients with OSA, even if asymptomatic, present special perioperative challenges. During the first three postoperative days, the risk of life-threatening apnea is increased in OSA patients due to the high levels of pain that mandate administration of analgesics (especially opioids). In the subsequent three postoperative days, REM sleep and deep slow-wave NREM rebounds, which again increases the risk of prolonged apneas during sleep. Therefore, patients who suffer from OSA appear to have two separate, sequential reasons for increased apnea during the week following surgery. See Rosenberg, J., G. Wildschiodtz, M. H. Pedersen, F. von Jessen, and H. Kehlet, in the article entitled "Late postoperative nocturnal episodic hypoxaemia and associated sleep pattern" published in the British Journal of Anaesthesia, 1994. 72(2): p. 145-50, Reeder, M. K., M. D. Goldman, L. Loh, A. D. Muir, K. R. Casey, and J. R. Lehane, in the article entitled "Late postoperative nocturnal dips in oxygen saturation in patients undergoing major abdominal vascular surgery. Predictive value of pre-operative overnight pulse oximetry" published in the British Journal of Anaesthesia, 1992. 7(2): p. 110-5, Reeder, M. K., M. D. Goldman, L. Loh, A. D. Muir, K. R. Casey, and D. A. Gitlin, in the article entitled "Postoperative obstructive sleep apnea. Haemodynamic effects of treatment with nasal CPAP" published in the British Journal of Anaesthesia, 1991. 46(10): p. 849-53, Reeder, M. K., M. D. Goldman, L. Loh, A. D. Muir, P. Foex, K. R. Casey, and P. J. McKenzie, in the article entitled "Postoperative hypoxaemia after major abdominal vascular surgery" published in the British Journal of Anaesthesia, 1992. 68(1): p. 23-6 and Rosenberg, J. and H. Kehlet, in the article entitled "Postoperative episodic oxygen desaturation in the sleep apnoea syndrome" published in Acta Anaesthesiol Scand, 1991. 35(4): p. 368-9.

The majority of the postoperative concerns in OSA patients are possible respiratory depression and hypoxemia following surgery. This may be potentiated by administration of systemic opioids for analgesia. Narcotics and sedatives suppress the brain's afferent output to pump muscles, such as the diaphragm and chest wall, resulting in inadequate tidal volume and associated fall in minute ventilation and a progressive rise in carbon dioxide levels. The rise in carbon dioxide levels causes further suppression of the arousal response, therefore, potentially causing respiratory arrest. Narcotics and sedatives also depress the brains afferent output to upper airway dilator muscles causing a reduction in upper airway tone.

In the early postoperative period, high pain scores, opioid consumption, and surgery itself may all contribute to a disruption of the normal sleep architecture. See Rosenberg-Adamsen, S., H. Kehlet, C. Dodds, and J. Rosenberg in their article entitled "Postoperative sleep disturbances: mechanisms and clinical implications" published in the British Journal of Anaesthesia, 1996. 76(4): p. 552-9, Cronin, A., J. C. Keifer, H. A. Baghdoyan, and R. Lydic, Opioid in their article "inhibition of rapid eye movement sleep by a specific mu receptor agonist" published in the British Journal of Anaesthesia, 1995. 74(2): p. 188-92, Keifer, J. C., H. A. Baghdoyan, and R. Lydic, in their article entitled "Sleep disruption and increased apneas after pontine microinjection of morphine" published in Anesthesiology, 1992. 77(5): p. 973-82 and Knill, R. L., C. A. Moote, M. I. Skinner, and E. A. Rose, in the article entitled "Anesthesia with abdominal surgery leads to intense REM sleep during the first postoperative week" published in Anesthesiology, 1990. 73(1): p. 52-61. The observed changes are sleep deprivation and fragmentation in the early days after surgery, REM sleep is usually absent on the first postoperative night, and sometimes even on the second and third postoperative nights. See Knill, R. L., C. A. Moote, M. I. Skinner, and E. A. Rose, in the article entitled "Anesthesia with abdominal surgery leads to intense REM sleep during the first postoperative week" published in Anesthesiology, 1990. 73(1): p. 52-61. Slow-wave sleep is also suppressed. Obstructive breathing is exacerbated in the late post-operative period as a result of a raised arousal threshold during deep non-REM sleep and the inherent breathing instability during REM sleep. In most patients, REM sleep subsequently reappears (rebound REM sleep) with increased intensity and duration, and REM-associated hypoxemic episodes increase about three-fold on the second and third postoperative nights compared with the night before surgery. See Knill, R. L., C. A. Moote, M. I. Skinner, and E. A. Rose, in the article entitled "Anesthesia with abdominal surgery leads to intense REM sleep during the first postoperative week" published in Anesthesiology, 1990. 73(1): p. 52-61 and Rosenberg, J., G. Wildschiodtz, M. H. Pedersen, F. von Jessen, and H. Kehlet, in their article entitled "Late postoperative nocturnal episodic hypoxaemia and associated sleep pattern" published in the British Journal of Anaesthesia, 1994. 72(2): p. 145-50. Sleep studies [8, 10-12], performed in patients undergoing major abdominal surgery and open heart surgery have shown that postoperative sleep patterns are disturbed severely by early depression of REM and slow wave sleep (SWS) in the early postoperative period, and by rebound of REM sleep and SWS in the late postoperative period. See Knill, R. L., C. A. Moote, M. I. Skinner, and E. A. Rose, in the article entitled "Anesthesia with abdominal surgery leads to intense REM sleep during the first postoperative week" published in Anesthesiology, 1990. 73(1): p. 52-61, Aurell, J. and D. Elmqvist, in the article entitled "Sleep in the surgical intensive care unit: continuous polygraphic recording of sleep in nine patients receiving postoperative care" published in the British Medical Journal (Clin Res Ed), 1985. 290(6474): p. 1029-32, Ellis, B. W. and H. A. Dudley, in the article entitled "Some aspects of sleep research in surgical stress" published in the J Psychosom Res, 1976. 20(4): p. 303-8 and Orr, W. C. and M. L. Stahl, in the article entitled "Sleep disturbances after open heart surgery" published in the American Journal of Cardiology, 1977. 39(2): p. 196-201. The rebound of REM sleep may contribute to the development of sleep-disordered breathing and nocturnal episodic hypoxemia. See Catley, D. M., C. Thornton, C. Jordan, J. R. Lehane, D. Royston, and J. G. Jones, in the article entitled "Pronounced, episodic oxygen desaturation in the postoperative period: its association with ventilatory pattern and analgesic regimen" published in Anesthesiology, 1985. 63(1): p. 20-8, Gentil, B., A. Lienhart, and B. Fleury, in the article entitled "Enhancement of postoperative desaturation in heavy snorers" published in Anesthesia Analgesia, 1995. 81(2): p. 389-92 and Reeder, M. K., M. D. Goldman, L. Loh, A. D. Muir, K. R. Casey, and J. R. Lehane, in the article entitled "Late postoperative nocturnal dips in oxygen saturation in patients undergoing major abdominal vascular surgery. Predictive value of pre-operative overnight pulse oximetry" published in Anaesthesia, 1992. 47(2): p. 110-5. Also REM rebound in the late postoperative period (at a time when oxygen therapy is likely to be discontinued and the patient discharged) may explain the finding that the highest perioperative mortality risk is not the day of surgery, or even the second day; it is on the third or fourth postoperative day. See Rosenberg, J., M. H. Pedersen, T. Ramsing, and H. Kehlet, in the article entitled "Circadian variation in unexpected postoperative death" published in the British Journal of Surgery, 1992. 79(12): p. 1300-2, which is herein incorporated by reference. The rebound of SWS can raise the arousal threshold, prolonging the time to arousal and allowing longer episodes of obstruction with deeper oxyhemoglobin desaturations.

The impact of OSA on patient safety is beginning to be recognized. See Deutscher, R., D. Bell, and S. Sharma, in the article entitled "OSA protocol promotes safer care" published in the Anesthesia Patient Safety Foundation Newsletter 2002-2003: p. 58. When compared to matched controls, orthopedic patients with OSA had more adverse outcomes. See Gupta, R., J. Parvizi, A. Hanssen, and P. Gay, in the article entitled "Postoperative complications in patients with obstructive sleep apnea syndrome undergoing hip or knee replacement: a case-control study" published in the Mayo Clinic Proceedings, 2001. 76: p. 897-905. Up to one-third of these patients developed substantial respiratory or cardiac complications, including arrhythmias, myocardial ischemia, unplanned ICU transfers and/or reintubation. The length of hospitalization was significantly longer for patients with OSA compared to the control subjects. For these orthopedic patients the majority of the cardiorespiratory or neuropsychiatric postoperative complications occurred within the first 72 hours after the joint replacement. The authors theorized that this might have been due to the combination of anesthetic agents, sedatives, and narcotics in conjunction with supine positioning during sleep postoperatively. Conversely, Sabers et al. found that OSA was not an independent risk factor for unanticipated hospital admission or for other adverse perioperative events in patients scheduled for outpatient surgery. These conflicting findings suggest that the type/invasiveness of surgery, which in turn may extend length of hospitalization, may contribute to the interaction between OSA and post-surgical complications.

Recent articles suggest that, at the present time, disastrous respiratory outcomes during the perioperative management of patients with obstructive sleep apnea are a major problem for the anesthesia community. See Benumof, J. L., in the article entitled "Obesity, sleep apnea, the airway, and anesthesia" published in Current Opinion in Anaesthesiology, 2004. 17(1): p. 21-30. The American Society of Anesthesiologists recently published Practice Parameters for the perioperative management of patients with OSA. See A Report by the American Society of Anesthesiologists Task Force on Perioperative Management of Patients with Obstructive Sleep Apnea, Practice Guidelines for the Perioperative Management of Patients with Obstructive Sleep Apnea, published in Anesthesiology, 2006. 104(5): p. 1081-1093. The purpose of the guideline was to improve perioperative care and reduce the risk of adverse outcomes in patients with OSA who receive sedation, analgesia, or anesthesia for diagnostic or therapeutic procedures under the care of an anesthesiologist. Unfortunately, due to a lack of medical evidence to guide the ASA recommendations, the practice parameters were based solely on expert opinion and are heavily reliant on the judgment of the anesthesiologist. Although there is an understanding of the broad categories of what increases the likelihood of developing a post-surgical complication, little is known about how individual risk factors interact to cause these complications. See Rock, P. and A. Passannante, in the article entitled "Preoperative assessment: pulmonary" published in Anesthesiology Clinics of North America, 2004. 22(1): p. 77-91, which is herein incorporated by reference. While several observations have led to considerable speculation in the literature as to the implications of sleep disturbance and sleep disordered breathing on perioperative morbidity and mortality, evidence of a causal relationship is still slight. See Loadsman, J. and D. Hillman, in the article entitled "Anaesthesia and sleep apnoea" published in the British Journal of Anaesthesia, 2001. 86(2): p. 254-266. Although OSA and anesthetic agents both produce significant changes in the respiratory system, little information exists regarding their relative contribution to the subsequent development of post-surgical complications, or the synergy between these and/or other risk factors such as the positional influence of OSA, type of anesthesia, use of opioids or invasiveness of the surgery.

A number of methods have been proposed to reduce the risk for postoperative complications. For example, Redmond proposed administering a drug or agent, such as methylol to a patient in conjunction with CPB surgery to reduce the risk for complications. See U.S. Pat. No. 6,641,571, issued Nov. 4, 2003. Turcott proposed monitoring respiration patterns to identify the presence of periodic breathing or Cheyne-Stokes respiration (i.e., recognize hyperventilation and apnea or hypoventilation) in patients with congestive heart failure. See U.S. Pat. No. 6,600,949, issued Jul. 29, 2003. This information may be used to warn the patient or healthcare provider of changes in the patient's condition that might result in a perioperative complication. Lynn proposed to automatically diagnose obstructive sleep apnea in a centralized hospital critical care or cardiac ward environment. In a preferred embodiment, the system would automatically identify the presence and severity of obstructive sleep apnea and communicate with an intravenous infusion system to prevent the progression of said identified obstructive sleep apnea by limiting infusion of a narcotic. Bardy proposed a method for an automated multiple near-simultaneous health disorder diagnosis and analysis, and, in particular, to an automated collection and analysis patient care system and method for ordering and prioritizing multiple health disorders to identify an index disorder. See U.S. Pat. No. 7,117,028, issued Oct. 3, 2006. These methods propose reducing the risk of complications via a means for monitoring or intervening, or identifying a patient with the pathophysiology corresponding to a heath disorder diagnosis. These methods differ from this invention which provides a means to identify those patients with an increased risk of perioperative complications, and provide physicians a method to reduce risk as a result of an intervention (change in sedative or narcotic, place on CPAP prior to surgery, etc).

There is no doubt that an integrated approach to the identification of patients at risk for perioperative complications will influence the practice of medicine. Advanced identification of patients at greater risk for perioperative complications will influence who administers an analgesic or, how, when and what sedative is administered. Prior identification of high risk patients can be used to determine the appropriate type of facility to be used for a given procedure (i.e., outpatient facility vs. hospital). Physicians can interactively model difference scenarios with the patient to assess changes in risk, making it easier for the clinician and patient to select the surgical option (i.e., nerve block vs. general anesthesia) which maximizes patient comfort and safety.

SUMMARY OF THE INVENTION

In one embodiment, a system and method is described, which can combine, for example, the acquisition of a patient's history and physical information, type and invasiveness of the surgery, type and dose of the intended sedative or narcotic, and level of OSA severity which can be derived from a questionnaire and/or a sleep study, for example; combined with a database of similar measures, for example; and, in one embodiment, automated analyses to predict the likelihood of perioperative complications and extended hospitalization. The resulting data can allow, for example, the system administrator to predict perioperative complications such as those that occur during administration of anesthesia, surgery, in the recovery room, on the medical/surgical ward, and result in readmission within a predetermined period, for example, 30 days.

In another embodiment, the system can predict the likelihood of perioperative complications such as those that occur during administration of anesthesia, surgery, in the recovery room, on the medical/surgical ward, and result in readmission within a predetermined period, for example, 30 days. The system provides a means for physicians and patients to input information to a database, and then through comparative analysis of patient data to database data identify risk levels or assess changes in risk level and as a result target interventions, such as the type and dosage of sedative or narcotic, and use of CPAP prior to surgery, in order to reduce the frequency and severity of complications.

In some embodiments, a statistical analysis, for example logistic step-wise regression analysis, is used to determine the relationships and interactions between perioperative complications and the various inputs (i.e., risk factors described below). One of the advantages of logistic regression analysis is that a likelihood of a correct classification can he computed for each variable included in the regression equation. Another advantage of logistic regression analysis is its capability to derive a propensity score from sets of predictive variables. This feature allows the predictive capability derived multiple variables to be isolated into a single measure, such that the predictive power from a limited size data set is not exceeded or over fitted. In other words, the practical application of "holding all other variables constant" can be achieved by incorporating the predictive capability of these variables into a propensity score and then developing a new logistic regression equation to model the changing variable. This feature is helpful given the plethora of risk factors and the need to isolate risk factors to make predictions based on case findings. In addition to logistic regression analysis, there are other statistical analyses that can be employed to derive probabilities or predict likelihood of events. As with any of the various statistical approaches that can be employed, the analysis begins with the database of data used to derive the predictive equations. One skilled in the art can appreciate how sets of predictive equations can be derived from a database of patient information to determine the risk likelihoods, and look up tables can be used to select recommendation/report messages proposed as outputs from the system.

In some embodiments, the methods and systems described above are implemented in a computer system. For example, the likelihood of perioperative complications for a given patient is obtained using sets of prediction equations derived from a patient population of data and incorporated into a software application that can be applied to an individual patient's data. Responses to the patient and physician data can be inputted via a computer input device and written to a database of patient responses. Alternatively, a web-based application could be used to input patient data to a database of patient information. In yet another embodiment the software application containing the prediction equations is executed on a computer with access to the patient's database of data and connected to an output device, for example a printer so that the prediction report can be printed. In a hospital environment, portable, handheld or wireless devices can be used to input or update patient and physician information to the patient's database. With access to the patient data, the prediction software could be operated from the portable, handheld or wireless device, providing immediate updated information that could be presented to the hospital staff via the LCD screen as the patient conditions which impact the predictive model(s) are updated. The sleep study data used to compute OSA severity can be downloaded, computed and written directly to the patient's database. The risk predictions can be immediately updated when the sleep data are acquired from additional sleep studies obtained during the perioperative period.

In one embodiment, the data from the patient's database and the outcomes from the surgery are updated to the population database. Routine additions to all inputs and outputs of the predictive model will allow the accuracy of the equations to be refined and improved. As the population database is expanded separate rules may be developed to account for special cases.

Other features and advantages of the present invention should be apparent from the following description which illustrates, by way of example, aspects of the invention.

DETAILED DESCRIPTION

Methods and Systems for prediction of risks for perioperative complications are described below. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Figure 1:
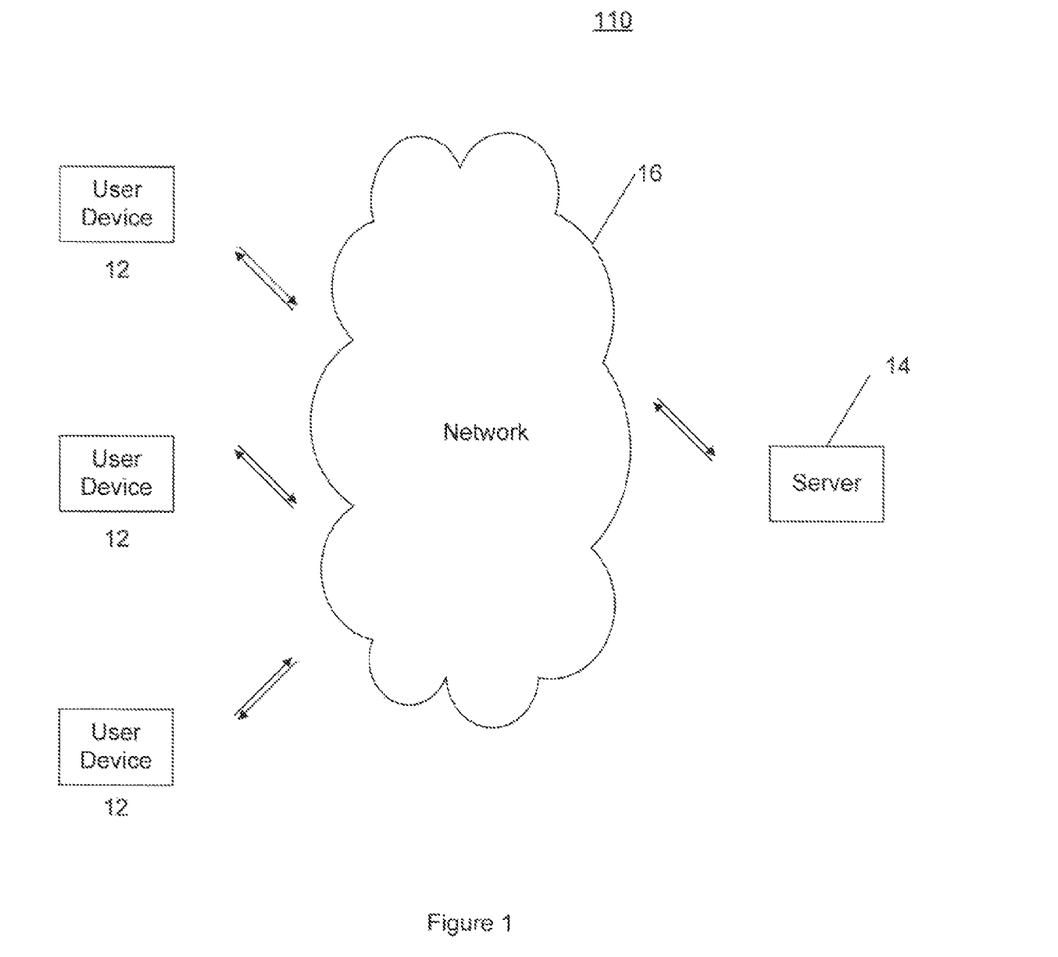
FIG. 1 is a schematic drawing of an exemplary network environment within which embodiments described herein can be implemented.

FIG. 1 is a schematic drawing of an exemplary network environment within which embodiments described herein can be implemented. Referring to FIG. 1 of the drawings, a network environment within which embodiments of the described technique may be practiced is indicated generally by reference numeral 110. Network environment 110 can accommodate a number of user devices 12 (only a few of which have been shown) each of which is able to communicate with a server 14 via a network 16. The network can be a wide area network (WAN) or local area network (LAN) using conventional network protocols or combinations of those. User devices 12 are electronic devices capable of communicating with the server 14 via the network 16. For example, user devices can be personal computers, cellular telephones, or other electronic devices capable of communicating over the network 16 directly or indirectly. A server can be one or more computers or devices on a network that manages network resources. A server can also refer to one or more programs managing resources rather than the entire computer.

Figure 2:
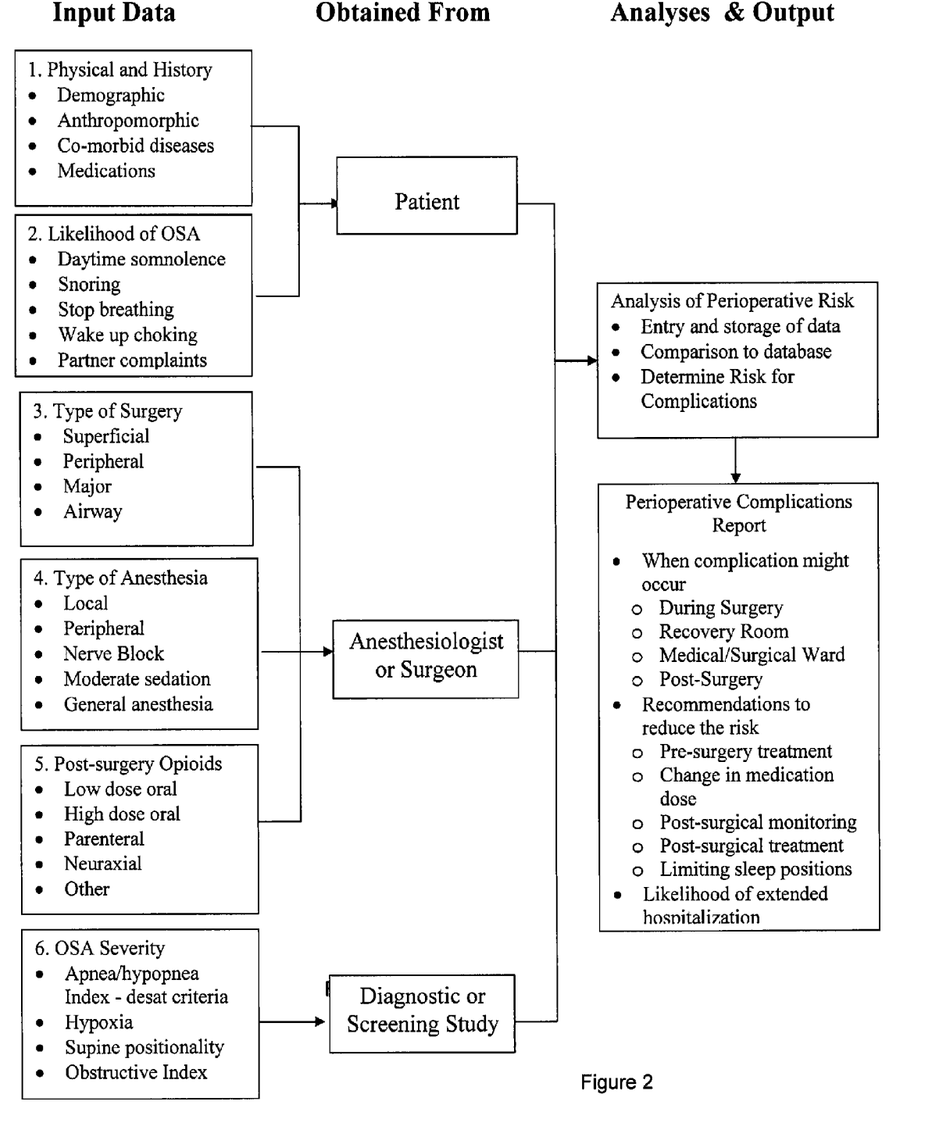
FIG. 2 illustrates a model, including list of factors upon which a system for predicting perioperative complications is based.

Inputs to the System:

FIG. 2 illustrates a model, including list of factors upon which a system for predicting perioperative complications is based. A system and method for predicting perioperative complications can be based on a number of risk factors that constitute the input to a patient database. The means used to acquire the necessary information and/or the risk factor may vary depending on the method employed. For example, the list of factors can be inputted via the user devices 12 illustrated and described in FIG. 1.

The input data can include demographic information such as age, gender, pre- or post-menopausal and ethnicity; anthropomorphic data such as weight, height, body mass index, neck or waist circumference, hip to waist ratio; and history of co-morbid diseases, such as hypertension, heart disease/congestive heart failure, chronic obstructive pulmonary (COPD) or other lung disease, diabetes or insulin insensitivity, stroke, pregnancy, sleep disorders, depression, or cancer; and current medications are all factors acquired during a pre-surgery history and physical because they are known to influence outcomes.

In addition to demographic, anthropomorphic, and co-morbidity data, patient responses as to the severity of symptoms of daytime somnolence, history of snoring, witnessed obstructive breathing during sleep or being awaken by obstructive breathing are commonly used to assess the prior-probability of OSA, either by clinical judgment or by statistical analysis. A number of questionnaires are currently available to assess daytime somnolence including the Epworth, Stanford, or Karolinka Sleepiness Scales. Structured questionnaires such as the Berlin test identify the severity and frequency of snoring, how often the patient is told they stop breathing during sleep, or how often they wake up in the night choking or struggling to breath (as a result of an apnea or hypopnea).

In clinical practice, these demographic, anthropomorphic and OSA related questionnaire responses should be acquired from the patient prior to surgery either as part of a pre-admission procedure or by the surgeon or primary-care physician. In the preferred embodiment, these data would be conveniently obtained using the Apnea Risk Evaluation system (ARES) Screener questionnaire. These data could be obtained by the patient using a written form of the Screener and entered or scanned into a computer system, for example the user device 12, or entered using a web-based application, and stored in a database of which an example is illustrated in FIG. 3 described below.

Another set of data that should be obtained in order to identify the risk of a perioperative complication are the invasiveness of the surgery, type of anesthesia, and type of opioid to be administered. All three of these risks are related and impact the length of hospitalization. For example, a non-laparoscopic abdominal surgery is invasive and usually requires general anesthesia and a 72-hour hospital stay. Some laparoscopic surgery could be performed with a regional or nerve blocking anesthetic with a short or no hospital stay. As the invasiveness of the surgery increases, so does the post-surgical dose and strength of the pain medication. In the preferred embodiment, these three risk factors are combined into a simple set of responses that could be easily assigned by a surgeon, anesthesiologist or primary care physician. A more refined means to categorize the surgery type can be performed using the International Statistical Classification of Diseases and Related Health Problems (ICD9) or current procedural terminology (CPT) code assigned by the physician and a reference table. Similar techniques can be used to allow physicians to select a specific type or from a menu of anesthesia or post-operative medication and dose to be administered by generic or brand name with a reference table used to assign this information into specific risk categories. These data could be obtained by the physician using a written form and entered into a computer via, for example the user device 12, or entered using a web-based application, and stored in a database.

A third set of data that would be beneficial in the identification of perioperative risk is the results from a diagnostic or screening OSA sleep study. In the preferred embodiment, the sleep study is conducted using the ARES Unicorder, a single site wireless recorder that is affixed to the forehead by the patient. It is used to acquire oxygen saturation, pulse rate, airflow, respiratory effort, snoring levels (dB), head movement and head position. Alternatively, electroencephalography, electromyography and electroccullargrams are acquired so that rebound in slow-wave (SWS) and rapid eye movement (REM) sleep that increases the risk of complications can be periodically monitored. Ideally the recorder monitors signal quality during use and alerts the patient what needs to be fixed to improve signal quality, preferable with verbal messages. Alternatively, a laboratory or in-home Polysomonography (Level I or II) study, limited channel (Level III) or screening (Level IV) study could be used to acquire any or all of these signals or other signals (i.e., ECG, etc) that may be used to assess sleep disordered breathing. See U.S. Pat. No. 7,117,028, issued Oct. 3, 2006. In some embodiments the assessment can also be acquired through the user device described in FIG. 1.

Figure 3:
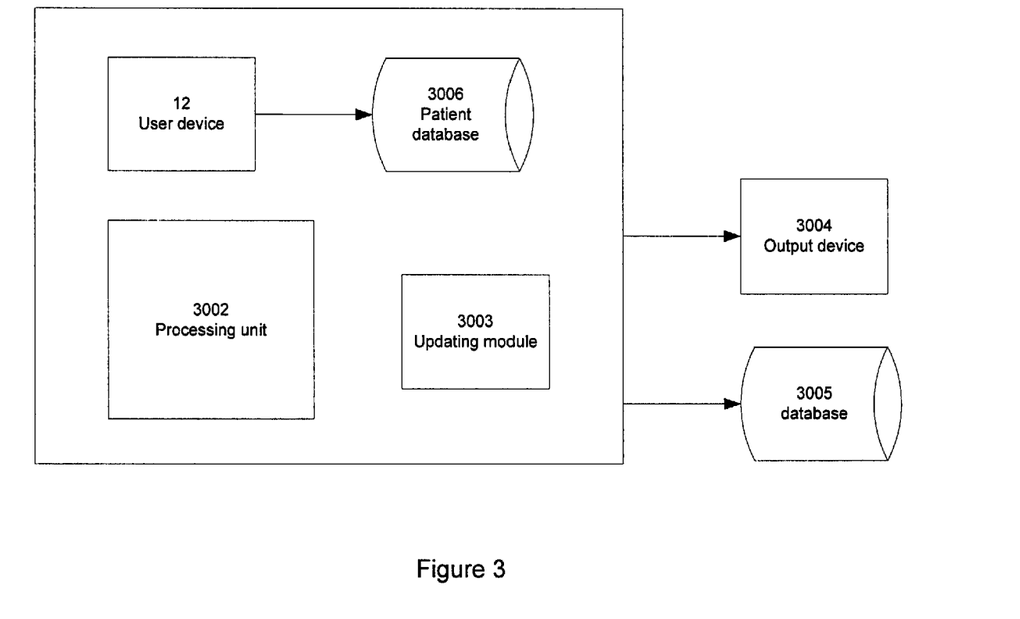
FIG. 3 is a block diagram illustrating aspects of an exemplary stand-alone computer system which implements embodiments of the invention.

FIG. 3 is a block diagram illustrating aspects of an exemplary stand-alone computer system which implements embodiments of the invention. The computer system can include a user device 12, which can have a user interface to input a set of risk factors, for example those illustrated in FIG. 2, that can be used to determine whether a patient is at risk of perioperative complications. In one embodiment user interface of the user device 12 can receive data or information via a keyboard or a touch pad, for example. Alternatively, a web-based application can be used to input the patient data to a database of patient information.

The computer system can also include a processing unit 3002 having a predictive model. The predictive model can incorporate one or more prediction equations for perioperative complications derived from one or more databases 3005 having multiple patient data relevant to predict perioperative complications. The databases can be a compilation of databases, in the same or different locations or a single database referred to as a population database. In general the one or more databases 3005 can be one or more existing databases from which relevant data to determine perioperative complications are accessed. In one embodiment, the system can include a patient database 3006 to store data received at the user device 12. The processing unit 3002 can be a part of the user device 12 or part of a separate computer system, or a server. For example, prediction software that incorporates the prediction equations can be operated from a portable, handheld or wireless device, providing immediate updated information. In some embodiments, the system includes an updating module 3003 to incorporate the set of risk factors for the patient, including surgical risk factors, and sleep study data of the patient into the predictive model in order to optimize the predictive model. The processing 3002 can assess changes in risk levels of perioperative complications for a patient and target intervention to reduce the frequency and severity of the perioperative complications as is described herein. Routine additions to all inputs and outputs of the predictive model will allow the accuracy of the equations to be refined and improved. As the population database is expanded separate rules may be developed to account for special cases. The system can be coupled to an output device 3004, for example, a printer or a monitor so that perioperative complications reports generated by the system can be outputted. The report can also be stored for offline analysis or utilized for real time monitoring.

Figure 4:
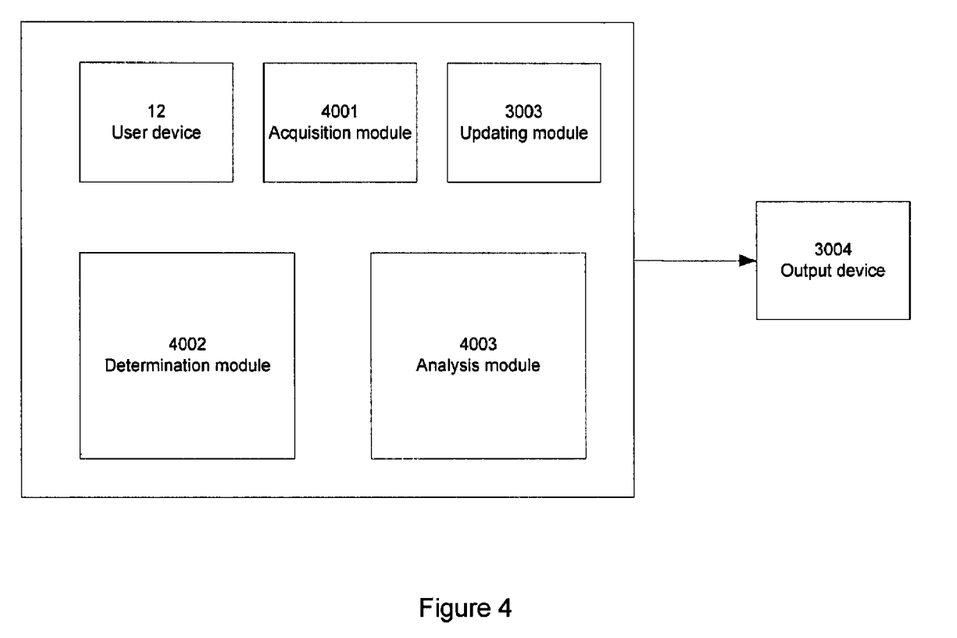
FIG. 4 is a block diagram illustrating aspects of an exemplary stand-alone computer system which implements embodiments of the invention.

FIG. 4 is a block diagram illustrating aspects of an exemplary stand-alone computer system which implements embodiments of the invention. The system for predicting risk for perioperative complications includes a user device 12 for receiving a set of risk factors to determine perioperative complications for a patient including patient data useful to determine the likelihood of obstructive sleep apnea. An acquisition module 4001 can be configured to receive data from an obstructive sleep apnea sleep study of the patient. In one embodiment the sleep study data can be conducted with the patient in various positions including the supine position. Also sleep study data can be acquired automatically and can be written to a sleep study database. In addition a determination module 4002 can determine the severity of obstructive sleep apnea for the patient. The determination module 4002 can score the data from the obstructive sleep apnea sleep study to determine the obstructive sleep apnea severity. The system can also include an analysis module 4003 having a predictive model that incorporates one or more prediction equations for predicting perioperative complications derived from one or more databases having multiple patient data relevant to predict perioperative complications, the analysis module 4003 configured to apply the one or more prediction equations to the set of risk factors and the severity of obstructive sleep apnea for the patient in order to identify perioperative complication risks of that patient and to generate a perioperative complications report for the patient. The perioperative complications report may include recommendations to reduce the frequency and severity of the perioperative complications. The report generated can be outputted to an output device 3004, for example, a printer or a screen. Some embodiments include an updating module 3003 to incorporate the set of risk factors for the patient, including surgical risk factors, and sleep study data of the patient into the predictive model in order to optimize the predictive model.

Figure 5:
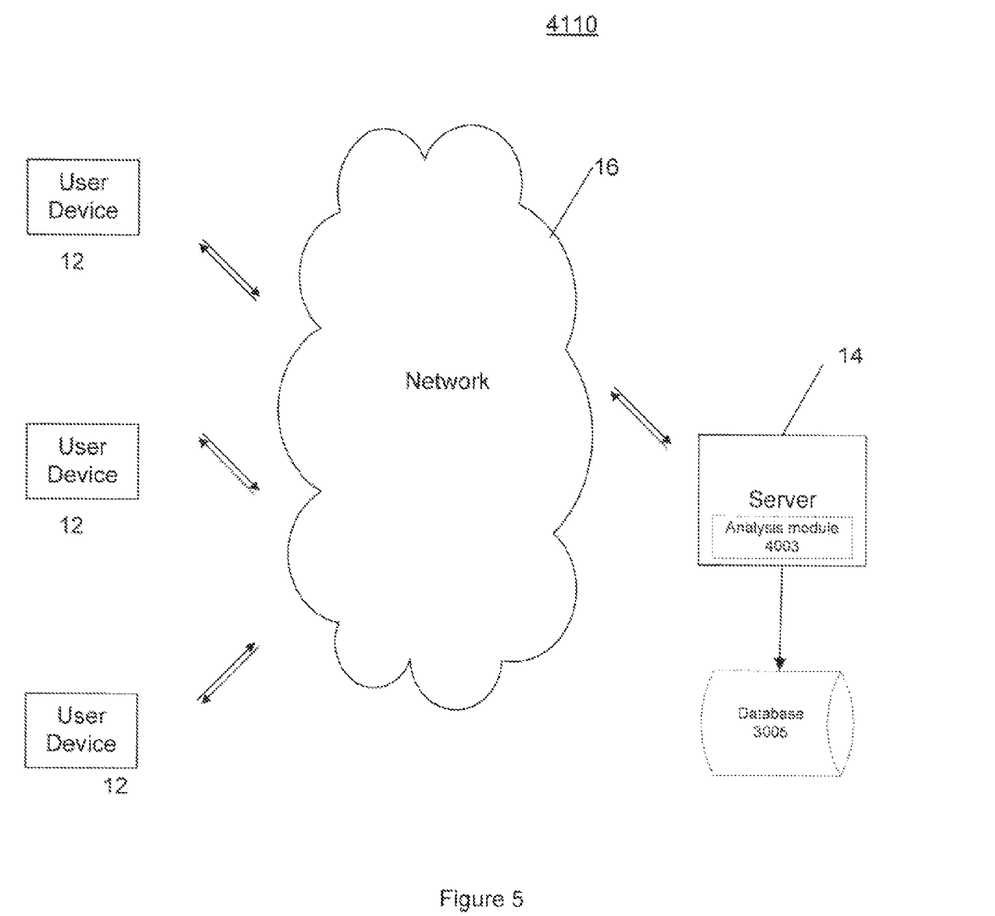
FIG. 5 is a block diagram illustrating aspects of an exemplary computer network system which implements embodiments of the invention.

FIG. 5 is a block diagram illustrating aspects of an exemplary computer network system which implements embodiments of the invention. In this embodiment the system is implemented in a network environment 4110 similar to the network environment illustrated in FIG. 1. The network environment 4110 can accommodate one or more users inputting patient data to the system. User devices provide the means for acquiring patient information or data. Each of the user devices 12 can communicate with a server 14 via a network 16. In one embodiment the user device 12 can include a user interface for receiving data via, for example a keyboard. A user can also communicate with the server 16 through the user interface which can be associated with a computer system or a process that requests service of another computer system or process, for example, a handheld or wireless device. A user can also communicate via, for example, one or more computers, a computer application or software such as a web browser that runs on a user's local computer or workstation and connects to a server as necessary or a combination of both. The server 14 can be one or more computers or devices on a network that manages network resources. In one embodiment the system can be configured with a database or data storage area 3005 that can be any sort of internal or external memory device and may include both persistent and volatile memories. The function of the database 3005 is to maintain data in for long-term storage and also to provide efficient and fast access to instructions for applications that are executed. The database 3005 can store a patient's data. When the database 3005 is used for the purpose of storing patient's data it can be referred to as the patient's database. The database 3005 can also be one or more databases some of which stores patient data and some of which store multiple patient data relevant to predict perioperative complications, for example a population database. In one embodiment the patient database is coupled to the user device 12. In another embodiment the population database is coupled to the server. However the databases are not limited to a particular location. In some embodiments, the server 14 includes an analysis module 4003 illustrated in FIG. 3 above. The analysis module 4003 can have a predictive model that incorporates one or more prediction equations for perioperative complications derived from one or more databases having multiple patient data relevant to predict perioperative complications, the analysis module configured to apply the one or more prediction equations to the set of risk factors for the patient to identify and report the likelihood of perioperative complication risks of that patient. The report generated can be a perioperative complications report. In another embodiment the system can be accomplished in a single computer system independent of a network.

After the sleep study data have been acquired, it is preferable that the signals are analyzed using automated, validated algorithms. That way the OSA severity can be immediately determined if the data were acquired the night before surgery or obtained routinely during hospitalization. Alternatively, the data could be scored and the OSA severity determined by visually inspection or a combination of automated scoring and visual inspection.

Figure 6:
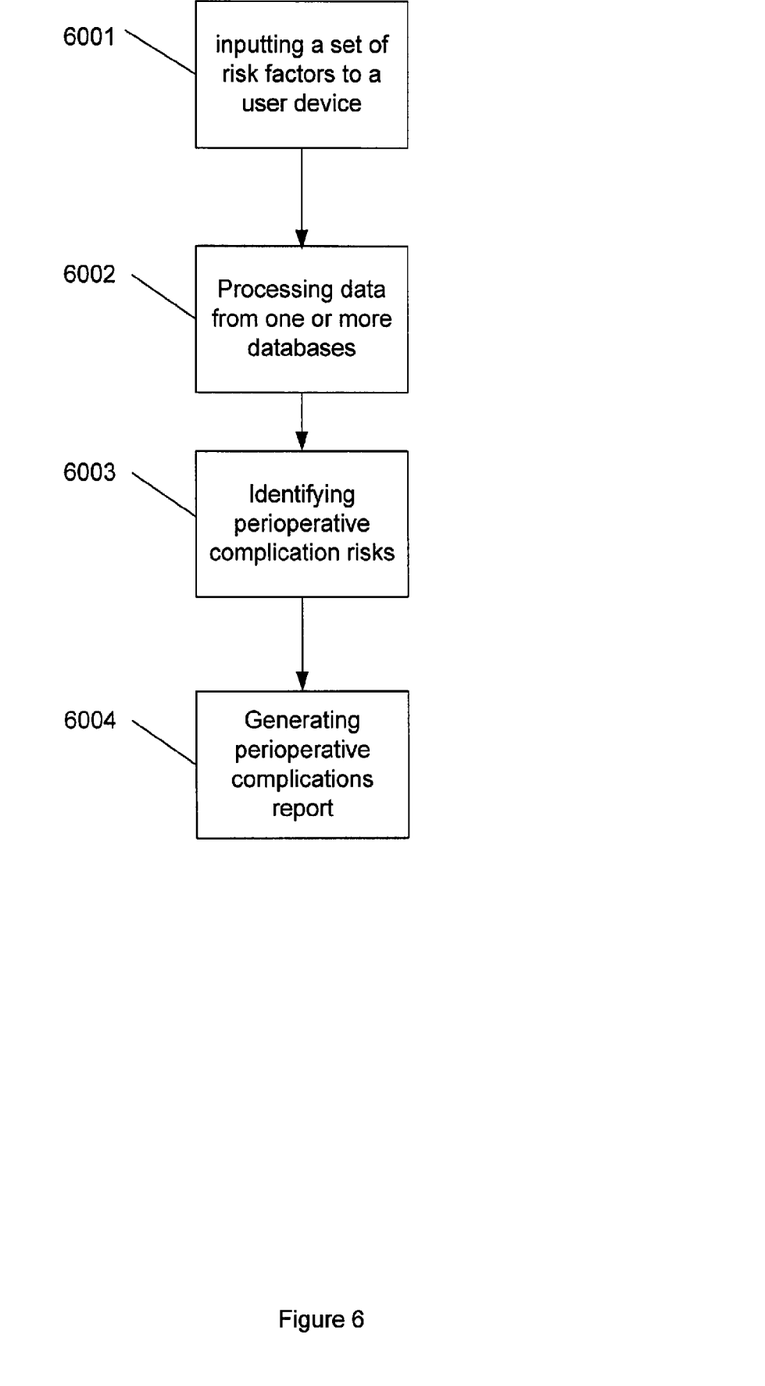
FIG. 6 is a flow diagram of a method for prediction of risk for perioperative complications.

FIG. 6 is a flow diagram of an exemplary procedure for prediction of risk for perioperative complications. The described procedure or method can be implemented using the systems described in connection with FIGS. 1, 3 and 4. In step 6001, the procedure starts with inputting patient data to, e.g., a user device illustrated in FIG. 3. This is the data described in connection with FIG. 2 above. The procedure then continues to step 6002, where data from one or more databases having multiple patient data relevant to predict perioperative complications is processed. The process can incorporate an analysis module, illustrated in FIG. 3 above, having a predictive model that uses one or more prediction equations derived from the data in the one or more databases and by applying the one or more prediction equations to the set of risk factors in order to predict perioperative complications risks for a given patient. In step 6003 risk levels of perioperative complications are identified. This step can also assess changes in risk levels of perioperative complications. The process then continues to step 6004, where a perioperative complications report is generated. The report can include recommended interventions to reduce the frequency and severity of the perioperative complications. In one embodiment the process can further include updating the risk predictions when new data is acquired from additional sleep studies obtained during the perioperative period.

In some embodiments, apneas (the cessation of airflow for at least 10 seconds), hypopneas (partial obstruction leading to oxygen desaturation or arousal), and prolonged obstructive breathing or hypoventilation events are differentiated and categorized. A patient who suffers from a complete cessation of breathing during sleep (apnea) as opposed to a partial obstruction will be at greater risk for post-surgical hypoxemia, assuming all other risk factors are held constant. Patients with prolonged obstructive breathing that normally does not manifest as unique obstructive breathing events (and are not normally counted in the AHI) may become more severe in the perioperative period, thus increasing the risk of complications. Patients who exhibit prolonged periods of hypoventilation (increased respiratory effort, loud or increased snoring, flow limitation and slow increase in desaturation) are particularly susceptible to post-surgical hypoxia. These distinctions can be incorporated into an algorithm at the processing unit illustrated in FIG. 3 or the server illustrated in FIG. 4 to streamline and improve the prediction system and method. In one embodiment the change in airflow associated with an apnea, hypopnea, obstruction or hypoventilation is based on flow amplitude. In an alternative measure, the required changes in airflow are identified by flow limitation. Alternatively, clinically significant changes in airflow could be detected by visual inspection.

In another embodiment, oxygen saturation is measured during the sleep study, preferably with a pulse-oximeter (i.e., SpO2) so that hypopneas are further stratified based on the depth of desaturation. This information can be incorporated into the list of factors describe in FIG. 2 and can also be used to update the prediction equations that are processed in the processing unit or server. A recent report linked the relationship between the body mass index, lung volume and the ability to desaturate. See Sasse, S. A., P. Westbrook, D. Levendowski, T. Zavora, R. Dalati, C. Vincent, and M. Popovic, in the article entitled "Timing of Changes in Oxyhemoglobin Saturation Resulting from Breath Holding" published in Sleep Medicine, 2006. 7 (S2): p. S46 (30). By way of example, an individual with a body mass index of 24 would desaturate on average 4% after holding his/her breath for 30-seconds at functional residual capacity, while an individual with a body mass index of 34 would desaturate approximately 10% in the same length of time. A relatively slim patient or pre-menopausal woman who desaturates less than 4% prior to surgery may experience significantly greater desaturation levels from sleep disordered breathing post-operatively as a result of a narcotics and sedative. Recent report suggest that multiple hypopnea criteria are very useful in predicting patients who will have a positive outcome with mandibular advancement therapy or in predicting the treatment pressure for fixed continuous positive airway pressure (CPAP). See Westbrook P, Levendowski D, Morgan T, Patrickus J, Berka, C, Olmstead R, Zavora T, Whitmoyer M, in "Predicting Treatment Outcomes for Oral Appliance Therapy for Sleep Apnea using Pre-treatment In-home Sleep Studies", $8^{th}$ World Congress on OSA and Westbrook P, Levendowski D, Henninger D, Nicholson D, Smith J, Zavora T, Yau A, Whitmoyer M, in "Predicting Effective Continuous Positive Airway Pressure (CPAP) based on Laboratory Titration and Auto-titrating CPAP", $8^{th}$ World Congress on OSA, both of which herein incorporated by reference. Alternatively simply counting the number of times or number of times per hour that the patient exceeds predefined thresholds of oxygen desaturation may be use to identifying the risk for perioperative complications.

When presenting SpO2 at 0.1% increments it is optimal to establish minimum desaturation and resaturation criteria to eliminate the counting of artifacts in the apnea/hypopnea index (AHI). For example, an AHI-4% hypopnea criteria can include a minimum 3.5% reduction in SpO2 (i.e., 3.5% rounds up to a 4% desaturation using integer presentations) and at least a 1.0% recovery. Hypopneas included in the AHI-3% and AHI-1% criteria can require SpO2 desaturation and resaturation using stepped thresholds. For the AHI-3%, if the SpO2 at the point of maximum saturation prior to the event was greater than or equal to 95% then a 2.2% reduction and a 2.2% recovery in SpO2 was required. For maximum saturations of between 95-93% the required SpO2 change is a 2.5% reduction and 2.5% recovery; between 93-91% a 3.0% reduction and 2.7% recovery; between 91-88% a 3.5% reduction and 3.0% recovery; and below 88% a 4.0% reduction and 3.5% recovery. For the AHI-1%, if the point of maximum saturation prior to the event was greater than 93% then a 1.0% reduction and 1.0% recovery is required; and for events with a starting SpO2 between 93-91%,a 1.2% reduction and 1.2% recovery is required. For an AHI-1% or AHI-0% (no desaturation) event to be called, it is beneficial to include confirmation by behavioral (i.e., an abrupt change in pulse rate, snoring sound or a head movement) or cortical arousals. One skilled in the art, however, can establish alternative desaturation thresholds or classification rules that utilize these elements in different combinations.

When measuring the blood oxygenation, the percentage of time SpO2 is less than 90% can identify patients with a greater likelihood of complications. Another measure of predictive hypoxemia is the average percentage drop in SpO2 as a result of sleep-disordered breathing. Some researchers have hypothesized that hypoxemia may result in increased sensitivity to opioid medication, thus patients who are hypoxic during sleep may require a lower dosage to achieve the same reduction in pain. The altitude at the location of surgery can influence the baseline oxygen saturation as well as the potential for the patient to experience increased hypoxemia when the respiratory system is suppressed.

In one embodiment, the sleep study result from processing data in the processing unit illustrated in FIG. 3 or the server illustrated in FIG. 4 includes a measurement of OSA severity (i.e., AHI, obstructive index, % time hypoxic, etc.) in the supine position. Because gravity influences the collapse of the pharynx the severity of OSA can be greater when a patient is on his/her back. After hip or knee surgery it's very common for patients to be hospitalized on their back for extended periods. Thus, the risk of post-surgical complications as a result of OSA is more directly related to the severity when supine as compared to the overall OSA severity in all positions.

The identification of patients with obstructive vs. central sleep apnea is also important in identifying the risk for post-surgical complications. A patient with obstructive breathing will present as a more difficult case during surgery (i.e., intubation and extubation). A patient with central sleep apnea typically stops breathing until a carbon dioxide in the lungs reach a level that triggers the brain to resume respiration. Thus, a patient with central sleep apnea would likely have having an underlying cause for the respiratory instability that might not yet be identified (i.e., congestive heart failure or stroke, intense pain, etc.). When central sleep apnea is identified, first the underlying cause should be identified because of its contribution to perioperative complications along with administering of supplemental O2 and monitored with pulse-oximetry to ensure the patient does not become hypoxic. For central sleep apnea, treatment by CPAP would not be appropriate or reduce the risk for complications. If an anesthesiologist is aware of the central apnea, he/she may choose to delay extubation in the recovery room.

The differentiation of obstructive and central apneas generally requires a combination of physiological signals can be useful to improve the prediction equations in the processed in the server of FIG. 4 or the processing unit of FIG. 3. The shape of the airflow signal may be used to identify changes in ventilation that are not obstructive (i.e., flattened inspiration). The most direct and invasive measure of respiratory effort is obtained by placement of an esophageal catheter via the nose or mouth but the most frequently used method is to record thoracic cage expansion. Typically bands are placed around the chest and abdomen, and the change in circumference of these two compartments with breathing is measured. Inductive plethysmography, piezo electric crystals, conductive elastomere, and polyvinylidine fluoride film, magnetometers and strain gages have all been used. Alternatively, a previously described embodiment that utilizes a non-invasive measure of forehead venous pressure by the mean of photoplethesmography (PPG) and/or a forehead pressure transducer can be used to measure respiratory effort (40). Finally, a quantified measure of snoring level (in decibels) can be used as a measure of respiratory effort and included as a means to differentiate patients with obstructive vs. central sleep disordered breathing. It is presumed that patients louder and prolonged snoring will have a greater likelihood of perioperative complications, consistent with the capability of quantified snoring to assist in the prediction of successful treatment of OSA with a mandibular advancement device. See Westbrook P, Levendowski D, Morgan T, Patrickus J, Berka, C, Olmstead R, Zavora T, Whitmoyer M; "Predicting Treatment Outcomes for Oral Appliance Therapy for Sleep Apnea using Pre-treatment In-home Sleep Studies", $8^{th}$ World Congress on OSA.

In one embodiment, the sleep study data used to predict the likelihood of perioperative complications is automatically written to a database, for example the patient database illustrated in FIG. 3. Rather than monitoring the patient continuously, sleep data can be gathered routinely or periodically to assess changes in OSA severity and the percentage of the sleep study with REM and SWS (to monitor for a rebound). When additional sleep studies are conducted during the post-surgery period, the database can be updated and a revised perioperative risk assessment computed. Alternatively, data obtained from continuous pulse-oximetry monitoring (i.e., time below 90% or standard deviation of the SpO2) or from a CPAP machine when worn during the perioperative period (i.e., CPAP pressure and AHI) can be used to update the risk of complications.

Outputs from the System:

The likelihood of perioperative complications can be predicted for each of five risk groups: 1) during induction of anaesthesia 2) during surgery, 3) in the recovery room, 4) while the patient is on the medical/surgical ward, and 5) post-surgery resulting in a significant change in morbidity and/or readmission to the hospital. Complications likely to occur during surgery include difficulty in intubation and extubation and hypoxemia. Recovery room complications include persistent transient events including but not limited to: a) hypoxemia (i.e., SpO2<90%) that requires supplemental oxygen to stabilize; b) high or low blood pressure; c) cardiac dysrhythmia which is new for the patient; d) aspiration pneumonia (with or without hypoxemia); and/or e) post-op atalectasis (hypoventilation and/or ventilation/profusion mismatch). Complications that occur while the patient is on the medical/surgical ward include: a) indications of shortness of breath or chest pain; b) a post-surgical chest x-ray abnormality; and/or c) an internist, pulmonologist, or cardiologist consultant was requested. Post-surgical complications include strokes, change in co-morbid conditions, or readmission for any reason within 30 days post-surgery. Likelihood ratios can be computed for each of these types of complication given a large database of patient data.

Other outputs from the system include data that can lead to recommendations that can reduce the likelihood of perioperative complications. The output from the system can be displayed or sent to an output device similar to that illustrated in FIG. 3. For example, initiation of treatment with CPAP is recommended for bariatric patients approximately one month prior to surgery to help to stabilize the patient's respiratory system and improve their immune system. Thus, the number of hours per night and the number of nights of CPAP use can interact to reduce the risk of perioperative complications. So if the predictive model includes updated information about CPAP time-on-pressure, the likelihood of complications can be updated. Patients who are non-compliant (i.e., less than 4 hours/night) would be expected to have a greater risk of complications than a compliant patient (all other factors held constant). The impact of a change in the type, dose and administration of a sedative or narcotic on perioperative risk can be determined when compared to a large database of similar case findings. The use of a computer- and data-based system as described above will allow a physician or healthcare provider to model different conditions to assess the optimal perioperative plan.

In addition to predicting the risk of OSA from processing data in the processing unit or server illustrated in FIGS. 3 and 4 respectively, those systems identify patients who require special monitoring post operatively. For example, a patient who suffers from hypoxia during sleep will have a greater likelihood of becoming hypoxic perioperatively. Thus, a referral to the intensive care unit for the recovery period and/or continuous monitoring by pulse-oximetry can be recommended by the system for the medical/surgical ward and/or during the patient's entire hospital stay. The report generated by the system can also advise the surgeon and hospital staff to carefully monitor the administration of narcotics since hypoxic patients may have a more sensitive dose-response curve. Patients with moderate or severe OSA can be recommended for CPAP while on the medical/surgical floor or immediately upon discharge. CPAP may also be recommended for patients with severe positional OSA who will have limited post-surgical positioning options. If the patient is identified with central or mixed obstructive/central sleep apnea, or the predicted CPAP pressure (38) is greater than 15, a bi-level CPAP may be recommended rather than a fixed- or auto-pressure CPAP to improve comfort and the likelihood of successful treatment.

The identification of moderate or severe supine-positional OSA in a patient who will have a surgery that limits their ability to be positioned laterally should result in the recommendation for continuous pulse-oximetry monitoring. Alternatively, an extended hospital stay can be recommended if continuous monitoring is required but would unavailable after the patient is discharged.

All of the risk factors and risk predictions derived from the systems or methods described above can be included in a report to be placed in the patient's medical record and/or provided to the patient. Thus, physicians and hospital administrators can notify the patient, his/her family and the insurer, in advance, so all stake-holders are aware of the perioperative risks and associated complications and recommendations to reduce risk. Advanced disclosure using an evidence-based process can be used to reduce the hospital and surgeon's exposure to liability if complications do occur and/or mitigate poor outcome scores that hospitals may receive when they serve the sickest patients.

The mere existence of a pre-operative evaluation system should be reassuring to the patient. The application of the system and interventions based on the information provided will provide evidence of care and interest by the surgical team in the patient's welfare during a time when patient may feel exceedingly vulnerable.

Those of skill in the art will appreciate that the various illustrative modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

The invention claimed is:
1. A system for predicting risk for perioperative complications comprising:
   a user device for receiving a set of risk factors to determine perioperative complications for a patient including patient data useful to determine the likelihood and severity of sleep apnea;
   an acquisition module to receive data from a sleep apnea sleep study of the patient, the data from the sleep apnea study including data collected while the patient was positioned in multiple sleep positions including a supine position;

a determination module to determine the severity of sleep apnea for the patient; and an analysis module having a predictive model that incorporates one or more prediction equations for predicting perioperative complications derived from one or more databases having multiple patient data relevant to predict perioperative complications, the analysis module configured to apply the one or more prediction equations to the set of risk factors and the severity of sleep apnea for the patient in order to identify and report the likelihood of perioperative complication risks of that patient.

2. The system of claim 1, wherein the set of risk factors are acquired from questionnaire responses, and the user device analyzes the questionnaire responses to determine if a patient is in need of a sleep apnea sleep study and the likelihood of that patient having mild, moderate or severe sleep apnea.

3. The system of claim 1, wherein the determination module is configured to score the data from the sleep apnea study to determine the sleep apnea severity.

4. The system of claim 1, wherein the sleep apnea study data is analyzed automatically and written to a sleep study database.

5. The system of claim 1, wherein the acquisition module is further configured to record the patient's head or body position while the sleep apnea study is being conducted.

6. The system of claim 1, further comprising an updating module to facilitate evaluation of the sets of risk factors, wherein the risk factors include surgical risk factors, in order to optimize the predicted likelihood of perioperative complications.

7. The system of claim 1, wherein the analysis module is further configured to generate a perioperative complications report, and wherein the perioperative complications report comprises recommendations to reduce the frequency and severity of the perioperative complications.

8. The system of claim 1, wherein the one or more databases comprises a population database.

9. The system of claim 1, wherein the determination module further monitors for a rebound of a sleep stage.

10. The system of claim 9, wherein the sleep stage comprises one or more of a rapid eye movement (REM) stage and a slow wave sleep (SWS) stage.

11. A system for predicting risk for perioperative complications comprising:

a user device for receiving a set of risk factors to determine perioperative complications for a patient; and a server comprising an analysis module having a predictive model that incorporates one or more prediction equations for perioperative complications derived from one or more databases having multiple patient data relevant to predict perioperative complications, the analysis module configured to apply the one or more prediction equations to the set of risk factors in order to identify and report the likelihood of perioperative complication risks of that patient.

12. The system of claim 11, further comprising an updating module to incorporate the set of risk factors, including surgical risk factors, and sleep study data of the patient into the predictive model in order to optimize the predictive model.

13. The system of claim 11, further configured to provide recommendations to reduce the frequency and severity of the perioperative complications.

14. The system of claim 11, wherein the risk factors are selected from the group comprising patient data, type and invasiveness of the surgery, type and dose of sedative or narcotic, likelihood of sleep apnea, level of sleep apnea severity, type of analgesics to be administered and type of anesthesia.

15. The system of claim 11, wherein the risk factors are written to a patient database.

16. The system of claim 11, further comprising an output device configured to output the report of the likelihood of perioperative complication risks of the patient.

17. The system of claim 11, wherein the user device is selected from the group consisting of a portable device, handheld device, a computer system, a web based application and a wireless device.

18. The system of claim 11, wherein the analysis module utilizes a statistical analysis to determine the relationship and interactions between perioperative complications and the set of risk factors, and generates the one or more prediction equations based on the statistical analysis.

19. A system for predicting risk for perioperative complications comprising:

a user device for receiving a set of risk factors to determine perioperative complications for a patient; and a processing unit having a predictive model that incorporates one or more prediction equations for perioperative complications derived from one or more databases having multiple patient data relevant to predict perioperative complications, the processing unit configured to apply the one or more prediction equations to the set of risk factors in order to identify and report the likelihood of perioperative complication risks of that patient.

20. A method for prediction of risk for perioperative complications comprising:

receiving a set of risk factors to determine perioperative complications into a user device;

processing data from one or more databases having multiple patient data relevant to predict perioperative complications by, incorporating in an analysis module having a predictive model, one or more prediction equations derived from the data in the one or more databases and by applying the one or more prediction equations to the set of risk factors in order to predict perioperative complications risks for a given patient;

identifying the likelihood of perioperative complications risks for a patient based on the processing; and generating a report of the likelihood of perioperative complications risk.

21. The method of claim 20, wherein the perioperative complications risk report comprises recommendations to reduce the frequency and severity of the perioperative complications.

22. The method of claim 20, further comprising incorporating the set of risk factors and sleep study data for the patient into the predictive model of the analysis module, wherein the risk factors include surgical risk factors.

23. The method of claim 20, further comprising:

periodically receiving data from a sleep apnea study of the patient; and applying the one or more prediction equations to the set of risk factors and the data from the sleep apnea study to predict the perioperative complications risks for the patient.

* * * * *